US007910141B2

(12) United States Patent
Segawa et al.

(10) Patent No.: US 7,910,141 B2
(45) Date of Patent: Mar. 22, 2011

(54) ANTIALLERGIC COMPOSITION

(75) Inventors: Syuichi Segawa, Yaizu (JP); Kazuhisa Yasui, Yaizu (JP); Nao Yasui, legal representative, Nagoya (JP); Toshio Kurihara, Yaizu (JP)

(73) Assignee: Sapporo Breweries Limited, Tokyo (JP)

( * ) Notice: Subject to any disclaimer, the term of this patent is extended or adjusted under 35 U.S.C. 154(b) by 102 days.

(21) Appl. No.: 11/817,620

(22) PCT Filed: Mar. 1, 2006

(86) PCT No.: PCT/JP2006/303889
§ 371 (c)(1),
(2), (4) Date: Mar. 7, 2008

(87) PCT Pub. No.: WO2006/093194
PCT Pub. Date: Sep. 8, 2006

(65) Prior Publication Data
US 2009/0028970 A1 Jan. 29, 2009

(30) Foreign Application Priority Data

Mar. 3, 2005 (JP) .................................. 2005-059714

(51) Int. Cl.
*A01N 65/00* (2009.01)
(52) U.S. Cl. ........................................................ 424/725
(58) Field of Classification Search .................. None
See application file for complete search history.

(56) References Cited

U.S. PATENT DOCUMENTS 5,972,411 A * 10/1999 Goldstein et al. ............. 426/600

FOREIGN PATENT DOCUMENTS

| AU | 2003-289063 | | 8/2004 |
|---|---|---|---|
| AU | AT 318606 T | | 3/2006 |
| CA | 2 368 574 | | 10/2000 |
| CN | 1726221 | | 1/2006 |
| DE | 60026279 D1 | | 4/2006 |
| EP | 1 172 109 A1 | | 1/2002 |
| EP | 1 577 315 A1 | | 9/2005 |
| JP | 48/44864 | | 12/1973 |
| JP | 06098738 | * | 4/1994 |
| JP | 09000227 | * | 1/1997 |
| JP | 2001-114686 A1 | | 4/2001 |
| JP | 3477628 | | 10/2003 |
| JP | 2004-052898 | | 2/2004 |
| WO | WO 00/57888 A1 | | 10/2000 |
| WO | WO 2004/52898 A1 | | 6/2004 |

OTHER PUBLICATIONS

Corchorus olitorius, 4 pages, 1983.*
Khan et al., Journal of Scientific and Industrial Research, vol. 65, 2006, 283-298.*
Walgren et al., 18, pages, 2000.*

Susumu Kitanaka, "Research Related to Development of Novel Natural Drugs Inhibiting Allergies", Health Sciences Research Grants (Immunity, Allergy, Etc.) Subject Report, vol. 2, 2003, pp. 267-275 (with English Translation).
A. Forster, et al., "On the Composition of Low Molecular Polyphenols in Different Varieties of HOPS and From Two Growing Areas", Monatsschrift Fuer Brauwissenschaft, vol. 55, No. 5 and 6, 2002, 1 Page (English Abstract).
A. Forster, et al., "Investigations on HOP Polyphenols", Proceedings of the Congress—European Brewery Convention, 1995, 1 Page (English Abstract).
J. Hubacek, et al., "Paper Chromatography of Flavanol Glycosides of HOPS", Collection of Czechoslovak Chemical Communications, vol. 29, No. 5, 1964, 1 Page (English Abstract).
R. Vancraenenbroeck, et al., "Characterization of Flavonols and Glucoside of Phloroisobutyro Phenone in HOPS", Proceedings of the Congress—European Brewery Convention, 1965, 1 Page (English Abstract).
Kunizo Kataoka, "New Diet Therapy", The Japanese Clinical Nutrition Association, vol. 19.9, 2003, 5 Pages (with English Translation).
Miho Takubo, et al., "Effects of HOP Extracts on Nasal Rubbing and Sneezing in BALB/c Mice", Biol. Pharm. Bull., vol. 29, No. 4, Apr. 2006, pp. 689-692.
Shuichi Segawa, et al., "Flavonoid Glycosides Extracted From HOP (*Humulus Lupulus L.*) As Inhibitors of Chemical Mediator Release From Human Basophilic KU812 Cells", Biosci. Biotechnol. Biochem., vol. 70, No. 12, 2006, pp. 2990-2997.
Shuichi Segawa, et al., "Effects of HOP Water Extract on the Compound 48/80- Stimulated Vascular Permeability in ICR Mice and Histamine Release From Ova-Sensitized BALB/c Mice", Biosci. Biotechnol. Biochem., vol. 71, No. 6, 2007, pp. 1577-1581.
Shuichi Segawa, et al., Clinical Effects of a HOP Water Extract on Japanese Cedar Pollinosis During the Pollen Season: A Double-Blind, Placebo-Controlled Trial, Biosci. Biotechnol. Biochem., vol. 71, 2007, pp. 70157-1-70157-8.
Toshihiko Ozawa, "New Functionality of Antioxidant Polyphenols", New Diet Therapy, vol. 19, 2003, pp. 79-81 and 169.
Hubacek, et al., "Papierchromatographie der Flavonol-Glykoside Des Hopfens (*Humulus Lupulus L.*)", Collection Czechoslov. Chem. Commun., vol. 29, No. 5, pp. 1259-1265, 1964 w/partial English translation of p. 1261, lines 28-33.
Li Guoli, et al., "A Study on the Antioxidation Activity of *Humulus Lupulus L.*", Journal of Ningxia Medical College, vol. 17, No. 1, pp. 27-29, 1995.
Hubacek, et al., "Papierchromatographie der Flavonol-Glykoside Des Hopfens (*Humulus Lupulus L.*)", Collection Czechoslov. Chem. Commun., vol. 29, No. 5, pp. 1259-1265, 1964.
Hubacek, et al., "Paper Chromatography of Flavonoids from Hops (*Humulus Lupulus L.*)", Collection Czechoslov. Chem. Commun., vol. 35, pp. 1595-1598, 1970.
Bartoszcze, et al. "Antiviral Properties of Plant Extracts Activity of Hop-D Cones Strobuli Lupuli-D", Bartoszcze M., Bulletin of the Verterinary Institute in Pulawy, vol. 12, No. 1-4, 1968, p69-p75.

* cited by examiner

*Primary Examiner* — Michael V Meller
(74) *Attorney, Agent, or Firm* — Oblon, Spivak, McClelland, Maier & Neustadt, L.L.P.

(57) ABSTRACT

The present invention provides an antiallergic composition that is moderate for the human body and skin, and has reduced side-effects; the antiallergic composition comprises a cold-water extract from hop tissue or flavonoid glycosides separated from the cold-water extract.

6 Claims, 8 Drawing Sheets

ANTIALLERGIC COMPOSITION

TECHNICAL FIELD

The present invention relates to an antiallergic composition.

BACKGROUND ART

Recently, some components contained in tealeaves are reported to have various beneficial effects on human. Increasing interest is being directed toward the antioxidant properties of polyphenols such as catechins, in particular (Non-patent document 1). It has also been reported that antioxidant components can be obtained by adsorption of the water-soluble fraction of hop bract onto gel-type synthetic adsorbents (Patent document 1).

[Patent document 1] Japanese Patent Publication No. 3477628

[Non-patent document 1] New Diet Therapy. Vo. 19, 9 (2003)

DISCLOSURE OF THE INVENTION

Problems to be Solved by the Invention

Human beings possess the immune system to protect themselves from the invasion of foreign substances such as bacteria, pollen, mites, and so on. The human bodies eliminate these antigens by producing antibodies and enhancing our lymphocyte responses against them. In some cases, however, overreactions to foreign substances were caused by the immune response. These overreactions are harmful to the body and trigger various diseases. Disorders caused by these overreactions are referred to as "allergies". Allergic disorder can be classified as immediate-type (type I-III) and delayed-type (type IV) based on its reaction mechanism.

Immediate-type allergic disorders, in which immunoglobulin E (IgE) antibodies play a crucial role, are frequently observed. IgE is produced by B cells, which respond to invading allergens. Cross-linking of IgE mediated by the binding of multivalent antigen at the surface of mast cells and basophiles triggers the release of many chemical mediators, such as histamine, serotonine from these cells. Type I allergic symptoms are induced by these chemical mediators. For example, skin rash (hives) accompanied with its redness and swelling caused by itching, runny nose, eye irritation, sneezing and bronchial asthma are induced by these chemical mediators.

These allergic disorders are usually treated with antispastic drugs, which relax smooth muscle, sympathomimetic drugs, which inhibit the increase of capillary permeability, or histamine release inhibitors. However, there is a risk of side effects caused by the ingestion of these drugs, because many of them are chemical synthetic drugs.

This invention was carried out to solve aforementioned problems of the prior art. The object of this invention was to provide an anti-allergic substance that has adequate safety and fewer side effects.

Means for Solving the Problems

Inhibitory effect of various food components on histamine release from human basophilic cells was investigated. As a result of this screening, the present investors have discovered that an extract obtained from hops have a property to inhibit histamine release, and the invention has been completed upon this discovery.

That is, the invention relates to an anti-allergic composition composed of a cold-water extract of hop tissue.

This antiallergic composition inhibits histamine release. For example, the oral administration of this antiallergic composition significantly inhibited the ear swelling caused by the immediate-type allergic reaction such as passive cutaneous anaphylaxis. This immediate allergic reaction was carried out as follows; mouse anti-DNP IgE antibodies were intradermally injected into mice auricle, and then antigen such as DNP conjugated human serum albumin (HSA) was injected into the caudal vein. Thirty minutes after the injection of antigen, ear thickness of mouse was measured, and the severity of immediate allergic reaction could be evaluated from the increase of ear thickness induced by this reaction. Moreover, since the antiallergic composition of this invention is an extract derived from natural hops, and the extraction process is carried out with cold water and does not requires any organic solvents, the risk of side-effects is low and the antiallergic composition can be used as an antiallergic drug that has an adequate safety for the human body and skin.

In Patent document 1 mentioned above, the hot water extract is obtained at 95° C. or 80° C. from the hop bract, but such a hot water extract exhibits virtually no antiallergic property, as demonstrated by the examples and comparative examples provided below. Furthermore, since the cold-water extract does not lose its antiallergic property even when heated, the active ingredients of the hot water extract and cold-water extract may be considered to be distinctly different.

In order to obtain a suitable extract for the antiallergic composition of the invention, a hop aimed at brewing is preferable to other hops and the hop tissue may be from stems, cones or leaves. The tissue may be a ground product of dried cones, preferably the ground product of dried cones from which at least a portion including lupulin and smaller components has been removed, and more preferably the ground product is from the dried bract.

Hops aimed at the brewing of effervescent alcoholic beverages such as beer are used in the form of hardened hop pellets obtained by drying of the cones (with the stems and leaves removed), grinding and then sifting through a sieve, with the ground product that fails to pass through the sieve being discarded. The discarded ground product is the ground product from which at least a portion including lupulin and smaller components has been removed, and because it consists mostly of the bract, a major contribution to reduction of industrial waste could be achieved and hop bract could be effectively utilized, by using this as a material for extraction of an antiallergic composition.

The ground product of the dried cones is also preferably a ground product of frozen dried cones. If the dried cones are frozen before grinding, the grinding efficiency will be increased and the effect of heat during grinding will be reduced, thereby allowing the antiallergic activity of the antiallergic composition in the ground product to be more stably maintained. Furthermore, since the ground product with the size of lupulin and smaller passes easily through the sieve, the purity of the ground product with a greater size than lupulin will be increased, thereby raising the purity of the antiallergic composition.

The tissue may also be hop residue obtained by removing at least a portion of the substances that are extracted by organic solvent extraction or supercritical fluid extraction from dried cones. Hop cones aimed at the brewing of effervescent alcoholic beverages such as beer are used as hop pellets and hop extract. The hop residue remaining after extraction of the hop extract is discarded. Because the discarded hop residue is obtained by removing at least a portion of the substances extracted by organic solvent extraction or supercritical fluid extraction, a major contribution to reduced industrial waste can be achieved by using this as a material for extraction of an antiallergic composition.

The cold-water extract mentioned above typically includes flavonoid glycosides. The flavonoid glycosides separated from the cold-water extract are responsible for an antiallergic property and can be used as an antiallergic drug. Such flavonoid glycosides preferably contain flavonol glycosides and the flavonol glycosides preferably include kaempferol glycosides. The keampferol glycosides include at least one selected from the group consisting of kaempferol rutinoside, astragalin and kaempferol malonylglucoside, and the antiallergic composition may further comprise quercetin malonylglucosides as flavonol glycosides. A flavonol is a compound having the structure of formula (1) below as its main nucleus.

[Chemical Formula 1]

(1)

Kaempferol glycoside has a skeleton represented by general formula (2) below. When $R_1$ is hydrogen and $R_2$ is a rutinose residue in general formula (2), it is kaempferol rutinoside. When $R_1$ is hydrogen and $R_2$ is a glucose residue, it is astragalin. When $R_1$ is hydrogen and $R_2$ is a malonylglucose residue, it is kaempferol malonylglucoside (astragalin malonic acid ester). When $R_1$ and $R_2$ are hydrogen in general formula (2), it is kaempferol, and when $R_1$ is an OH group and $R_2$ is a malonylglucose residue, it is quercetin malonylglucoside (isoquercitrin malonic acid ester).

[Chemical Formula 2]

(2)

It has been reported that flavonol glycosides could be absorbed from the gastrointestinal tract as a glycoside or hydrolyzed in the gastrointestinal tract and absorbed as the free form (aglycone) when orally ingested, (Rinsho Eiyo, Vol.102, No.3, 285 (2003)). Flavonoid glycosides such as kaempferol (or quercetin ) are hydrolyzed and absorbed as their aglycones.

Effect of the Invention

According to the invention, there is provided an anti allergic composition with an excellent inhibiting effect against release of pharmacologically active amines such as histamine and serotonin from mast cells and basophils, for prevention of or alleviation of the symptoms of allergic conditions such as pollen hypersensitivity. Because the anti allergic composition of the invention is derived from a natural plant, side-effects can be reduced to a satisfactory level and the antiallergic composition is moderate for the human body and skin.

BRIEF DESCRIPTION OF THE DRAWINGS

FIG. 7 shows the effect of the hop-cold water extract on the increase of ear thickness of mouse induced by a passive cutaneous anaphylaxis. This immediate allergic reaction was carried out as follows; mouse anti-DNP IgE antibodies were intradermally injected into mice auricle, and then antigen such as DNP conjugated human serum albumin (HSA) was injected into the caudal vein. Thirty minutes after the injection of antigen, ear thickness of mouse was measured, and the severity of immediate allergic reaction could be evaluated from the increase of ear thickness induced by this reaction.

BEST MODE FOR CARRYING OUT THE INVENTION

The hop varieties aimed at beer brewing such as Czech Saaz, German Hallertauer Tradition or Kokusan Furano #18 are suitable for this invention.

The flavonol content differs depending on the hop variety, and Czech Saaz is preferably used to obtain a hop extract with high anti allergic activity. The hop tissue used for extraction may be hop leaves, cones or stems. The spent hops obtained during processing of the cones or concentrated hop pellets, or the residue from carbon dioxide gas extraction (supercritical extraction), may also be used.

The antiallergic composition of the invention is the cold water extract from the above mentioned hop tissues, where "cold water" is defined as water at a temperature below room temperature. The temperature of the cold water is preferably above 0° C. and no higher than 50° C., and normally it will be from 0-30° C. The temperature of the cold water is more preferably from 0-10° C., and even more preferably 5±3° C. (especially 5±2° C.). In order to increase the extraction efficiency and shorten the extraction time, a small amount of alcohol, preferably ethanol, may be added at no greater than 10 wt % to the cold water.

If the extraction water is colder than 0° C. the extraction will be hampered due to freezing, and if the water is not cold (for example, if its temperature is above 50° C.), the antiallergic activity will be significantly reduced, rendering the extract unsuitable for use.

The cold-water extraction of the hop tissue is carried out by an ordinary method. For example, the hop pellets and water are placed in a container and allowed to stand for a prescribed time with appropriate stirring. The solution obtained after standing may be utilized directly as a cold-water extract, or the supernatant obtained from centrifugation of the solution (hereinafter referred to as "centrifugal supernatant") may be collected for use as the cold-water extract. Alternatively, the water may be removed from the solution obtained after standing or the centrifugal supernatant, and the dried residue used as the cold-water extract.

The active ingredient of the antiallergic composition of the invention is preferably a cold-water extract of the ground product of dried hop bract, and more preferably the active ingredient is the cold-water extract from the ground product of dried hop cones with at least a portion of the ground product including lupulin and smaller components removed. The ground product of dried cones used for the cold-water extraction may be obtained, for example, by a production process comprising a drying step in which the hop cones are dried to obtain dried cones, a grinding step in which the dried cones are ground to obtain a ground product, and a separating step in which the portion of the ground product with the size of lupulin and smaller is removed from the ground product.

In the drying step, the hop cones may be dried at a temperature of 100° C. or below and the water removed to an extent allowing preservation of the cones, but preferably the drying is carried out at a temperature of no higher than 55° C. to a water content of 7-9%. The grinding step accomplishes efficient fine grinding of the dried cones obtained in the manner described above, and a pulverizer such as a pin mill, hammer mill, ball mill or the like may be used. In the separating step, the ground dried cones are sifted to obtain the ground product with a long diameter of, for example, 0.1 mm or greater as a "size larger than lupulin". In this case, the size that fails to pass through the sieve is preferably a long diameter of 0.3 mm or greater, and more preferably a long diameter of 0.5 mm or greater. In order to remove the portion of the dried cone ground product having a size no larger than lupulin, the dried cone ground product may be sifted using a sieve with an aperture of 0.1, 0.3 or 0.5 mm, for example, and recovering the ground product that fails to pass through the sieve. The cold-water extraction of the ground product of dried cones from which at least a portion including lupulin and smaller components has been removed may be carried out by the process described above.

The ground product of dried hop cones used to prepare the antiallergic composition of the invention is preferably a ground product from frozen dried cones. The method for freezing the dried cones is not particularly restricted but is preferably carried out at −10° C. or below, and more preferably −35° C. or below.

The active ingredient of the antiallergic composition of the invention may be a cold-water extract of hop residue obtained by removing at least a portion of the substances that are extracted by organic solvent extraction or supercritical fluid extraction from dried hop cones. As examples of organic solvents to be used for organic solvent extraction there may be mentioned alcohols or hexane, among which C1-4 lower alcohols are preferred and ethanol is most preferred. As examples of supercritical fluids to be used for supercritical fluid extraction there may be mentioned carbon dioxide, water, methane, ethane, ethylene, propane, pentane, methanol and ethanol, among which carbon dioxide is preferred.

Further separation of the cold-water extract from the hop tissue can yield a flavonoid glycoside, which itself may be applied as an antiallergic composition. Preferred examples of separation methods will now be explained. First, a step is carried out in which the cold-water extract is contacted with hexane to obtain a first extract in an aqueous phase (hereinafter referred to as "first step"), and then a step is carried out in which the first extract is contacted with ethyl acetate to obtain a second extract in the aqueous phase (hereinafter referred to as "second step"). This is followed by a step in which the second extract is contacted with a poorly water-soluble alcohol (meaning an alcohol that fails to mix with water up to a specified proportion) and preferably a C4-5 alkanol, especially butanol), to obtain a third extract (hereinafter referred to as "third step"), whereby a flavonoid glycoside is obtained.

In the first step, the hop extract which is not the desired active ingredient (flavonoid glycosides, etc.) elutes into the hexane and is selectively removed from the cold-water extract. The method of contacting the cold-water extract with the hexane may involve, for example, placing the centrifugal supernatant and hexane in a separatory funnel and then shaking the separatory funnel to contact the cold-water extract and hexane. After contacting the cold-water extract and hexane, the separatory funnel is allowed to stand for separation of the aqueous layer and hexane layer, and the aqueous layer is used in the second step.

In the second step, the first extract obtained in the first step is contacted with ethyl acetate. This accomplishes extraction of the portion of hop extract other than the desired active ingredient into the ethyl acetate. The method of contacting the first extract with the ethyl acetate may involve, for example, placing the first extract and ethyl acetate in a separatory funnel and then shaking the separatory funnel to contact the first extract and ethyl acetate. After contacting the first extract and ethyl acetate, the separatory funnel is allowed to stand for separation of the aqueous layer and ethyl acetate layer, and the aqueous layer is used in the third step.

In the third step, the second extract obtained in the second step is contacted with a poorly water-soluble alcohol to obtain a flavonoid gylcoside. The method of contacting the second extract with the poorly water-soluble alcohol may involve, for example, placing the second extract and poorly water-soluble alcohol in a separatory funnel and then shaking the separatory funnel. The separatory funnel is then allowed to stand for separation of the aqueous layer and the poorly water-soluble alcohol layer, with the flavonoid glycoside residing in the poorly water-soluble alcohol layer. In order to obtain a greater flavonoid glycoside yield, the third step may be repeated several times, and preferably 2-4 times.

The flavonoid glycoside may be separated by passing the cold-water extract of the hop tissue through a column packed with a synthetic adsorbent (as examples there may be mentioned synthetic adsorbents such as Amberlite XAD-4, 7 and 16 (trade names of Organo Co., Ltd.), active carbon and polyvinylpolypyrrolidone (PVPP; polyphenol adsorbent), among which XAD-4 is preferred). Specifically, the cold-water extract of the hop tissue is passed through a column packed with a synthetic adsorbent and the adsorbed components are eluted into a mixed solvent of water and methanol to obtain the flavonoid glycosides.

The antiallergic composition of the invention can be used to prevent or alleviate the symptoms of a variety of allergic diseases including atopic dermatitis, bronchial asthma, allergic rhinitis, angioedema, atopic disease, allergic contact dermatitis, pollen hypersensitivity, hives and the like. That is, it exhibits a function as an antiallergic composition.

Because the antiallergic composition of the invention exhibits a histamine release inhibiting effect and an auricular edema-inhibiting effect, it is most preferably used to prevent or alleviate the symptoms of atopic dermatitis, contact dermatitis and pollen hypersensitivity. In order to prevent or alleviate the symptoms of such conditions, it may be prepared as a drug, and especially as a prophylactic or treatment agent for atopic dermatitis, contact dermatitis or pollen hypersensitivity.

Also for the purpose of preventing or alleviating the symptoms of atopic dermatitis, contact dermatitis or pollen hypersensitivity, it may be included as a food additive in foods or beverages such as specific hygienic foods, special nutritive food products, nutritional supplements, health foods, functional foods, patient foods and the like, or as a cosmetic additive in cosmetics such as skin care products, foundations and makeup products.

EXAMPLES

The present invention will now be explained in greater detail through examples, with the understanding that the invention is in no way limited to the examples. Unless otherwise specified, "%" refers to "wt %".

Example 1

Cold-water Extraction from Hop Leaves:

Hop leaves (Kokusan Furano #18) were chopped and immersed in a 10-fold amount (w/v) of water, after which the mixture was allowed to stand overnight at 5° C. and centrifugally separated at 7000 rpm for 15 minutes, and the supernatant was recovered to obtain a cold-water extract.

Identification of cold-water extract:

The supernatant was transferred to a separatory funnel, hexane was added and the hexane-migrating components were discarded. Ethyl acetate was then added to the aqueous layer, and the ethyl acetate-migrating components were discarded. Finally, n-butanol was added to the aqueous layer, and the butanol layers obtained by repeating butanol extraction three times were combined and concentrated under reduced pressure to obtain a flavonol fraction (flavonoid glycosides separated from cold-water extract from hop tissue).

The obtained flavonol fraction was first analyzed by high performance liquid chromatography (HPLC). The HPLC analysis was carried out using a C18 column (Waters Symmetry) at 40° C., with a flow rate of 0.2 mL/min. The mobile phase was a linear gradient with 0.05% TFA/$H_2O$ as solution 1 and acetonitrile as solution 2, varying the proportion of the two solutions from 10%-50% over a period of 16 minutes. Detection was carried out with a 350 nm UV detector.

Each peak of the flavonol fraction was separated by preparative HPLC and the components of each peak were identified. The fractional separation by HPLC was carried out using a C18 column (Waters SunFire) at 40° C., with a flow rate of 6 mL/min. The mobile phase was a linear gradient with 10% MeCN held for 10 minutes and then varying to 60% MeCN over a period of 150 minutes. Detection was carried out with a 350 nm UV detector. The results of HPLC are shown in FIG. 1.

Figure 1:
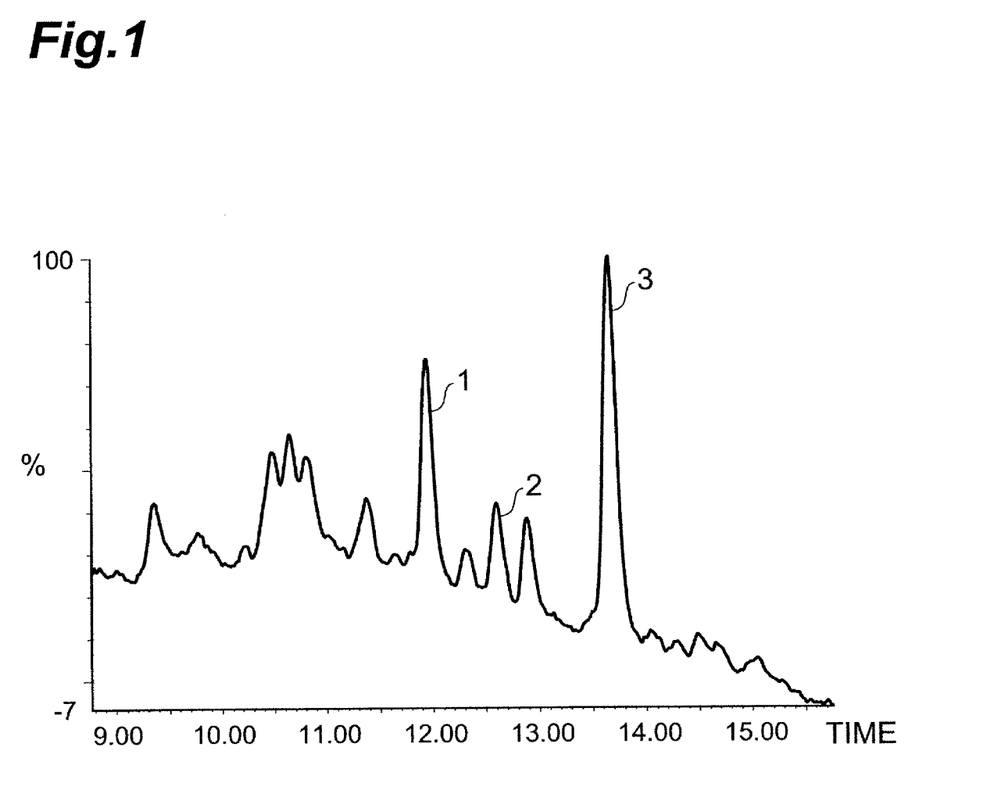
FIG. 1 shows an HPLC chromatogram of the flavonol fraction extracted from hop leaves with water (Kokusan Furano #18).

As shown in FIG. 1, three main peaks are observed in the flavonol fraction of the hop leaf extract, and all three were identified as kaempferol glycosides. Specifically, peak 1 in FIG. 1 is kaempferol rutinoside, peak 2 is astragalin and peak 3 is kaempferol malonylglucoside. Quercetin glycosides, such as quercetin malonylglucoside, were essentially undetected.

Example 2

Cold-water Extraction from Hop Pellets:

After placing 1 kg of hop pellets (Czech Saaz: type 90) in 10 L of distilled water, the mixture was allowed to stand overnight at 5° C. while occasionally stirring to eliminate the pellet form. It was then centrifuged at 7000 rpm for 15 minutes and the supernatant was recovered and concentrated to obtain 150 g of a cold-water extract.

Figure 2:
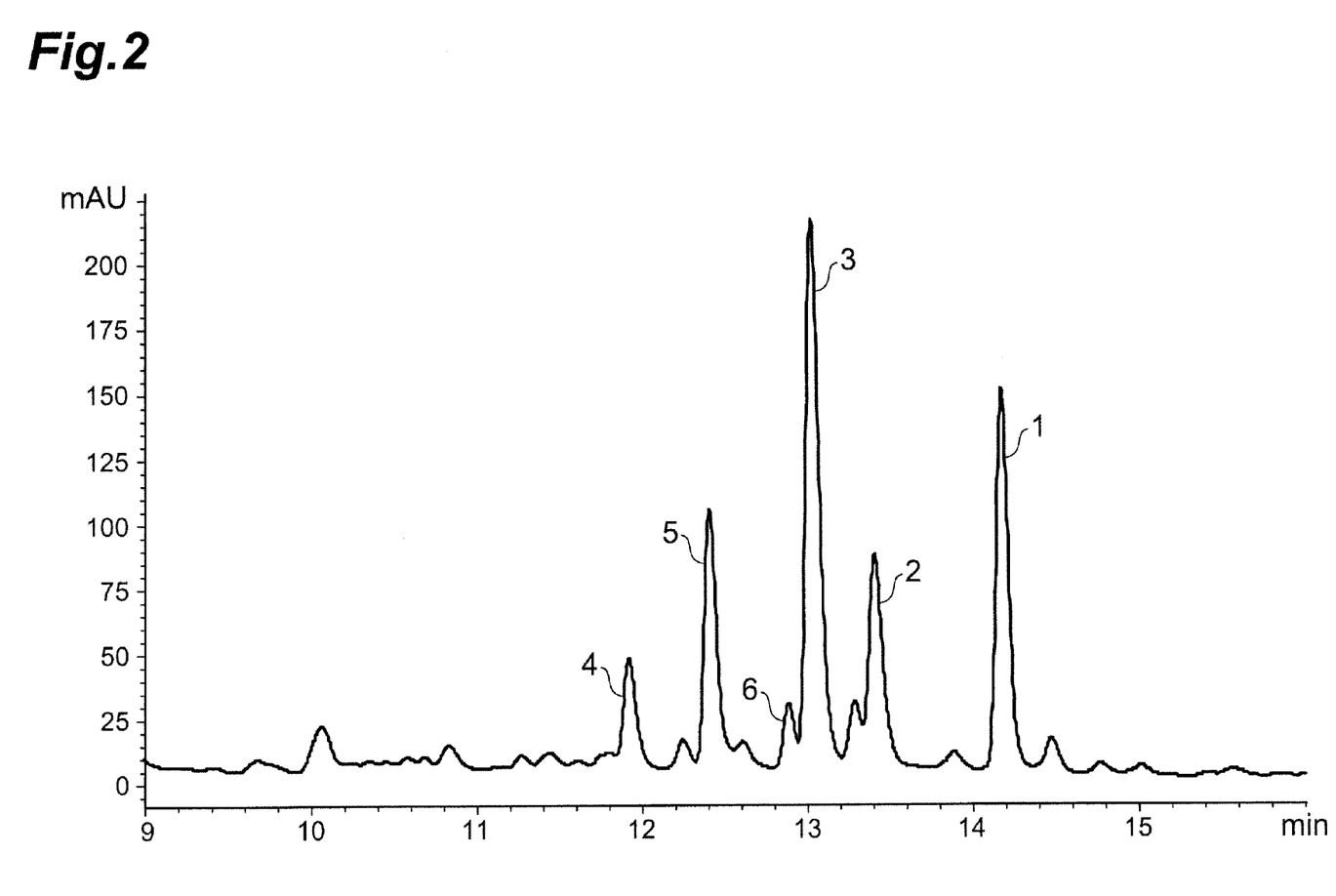
FIG. 2 shows an HPLC chromatogram of the flavonol fraction extracted from hop pellets with water (Czech Saaz).

Identification of cold-water extract:

The butanol extraction component of the supernatant was obtained by the same method as Example 1, and HPLC analysis was conducted to identify the component. The results of HPLC are shown in FIG. 2. As shown in FIG. 2, three main peaks are observed in the flavonol fraction of the hop pellets extract, and they were identified as kaempferol glycoside (astragalin and kaempferol malonylglucoside) and quercetin malonylglucoside. Specifically, peak 1 in FIG. 2 is kaempferol malonylglucoside, peak 2 is astragalin and peak 3 is quercetin malonylglucoside. Peak 4 in FIG. 2 is rutin, peak 5 is isoquercitrin and peak 6 is kaempferol rutinoside.

Comparative Example 1

Hop pellets (Czech Saaz: type 90) were extracted with a chloroform-methanol solution (chloroform:methanol=3:1) to 1% (w/w). The extraction was carried out for 2 hours at the boiling point of the chloroform-methanol solution. The yield was approximately 15%.

Comparative Example 2

Hop pellets (Czech Saaz: type 90) were extracted for 2 hours with boiling water to 1% (w/w). The yield was approximately 23%.

Confirmation of histamine release inhibition by hop extract:

The hop extracts obtained in Example 2 and Comparative Examples 1-2 were used in the following manner to confirm the histamine release inhibition.

An established human basophil cell line (KU812) was cultured at 37° C. under 5% $CO_2$ using RPM11640 medium (Gibco) containing 10% fetal calf serum inactivated at 56° C. for 30 minutes. After rinsing the cells twice with Tyrode solution, they were suspended in Tyrode solution and dispensed in a 1.5 mL volume tube to $2\times10^6$ cells/mL. To the cell suspension there was added a buffering solution in the amount shown in Table 1, 10 mM $CaCl_2$, 50 µM A23187 and/or a test sample (hop extract), and after histamine release reaction at 37° C. for 20 minutes, it was placed in ice for 5 minutes to suspend the reaction.

TABLE 1

|  | Total intracellular histamine | Natural release (negative control) | A23187 (positive control) | Test sample |
|---|---|---|---|---|
| 10 mM $CaCl_2$ | — | 110 µl | 110 µl | 110 µl |
| 50 µM A23187 | — | — | 110 µl | 110 µl |
| Test compound | — | — | — | 110 µl |
| Buffer solution | 600 µl | 490 µl | 380 µl | 270 µl |
| Cell suspensions | 500 µl | 500 µl | 500 µl | 500 µl |

After centrifugation at 4° C., 1000 rpm for 3 minutes, the supernatant was collected. The released histamine was extracted from the collected supernatant with an organic solvent and reacted with o-phthalaldehyde, and the intensity of the emitted fluorescence was measured at a wavelength of 450 nm after excitation with light with a wavelength of 350 nm, for quantitation of the released histamine. The total intracellular histamine was determined by ultrasonic disruption of an equivalent amount of cell suspension in ice for 1 minute, followed by measurement of the histamine content of the supernatant obtained by centrifugation at 4° C., 10,000 rpm for 3 minutes. The histamine release inhibition (%) was determined by the formula: 100-{(histamine content of supernatant for each sample−natural release)×100/(histamine release by stimulation with A23187−natural release)}.

Figure 3:
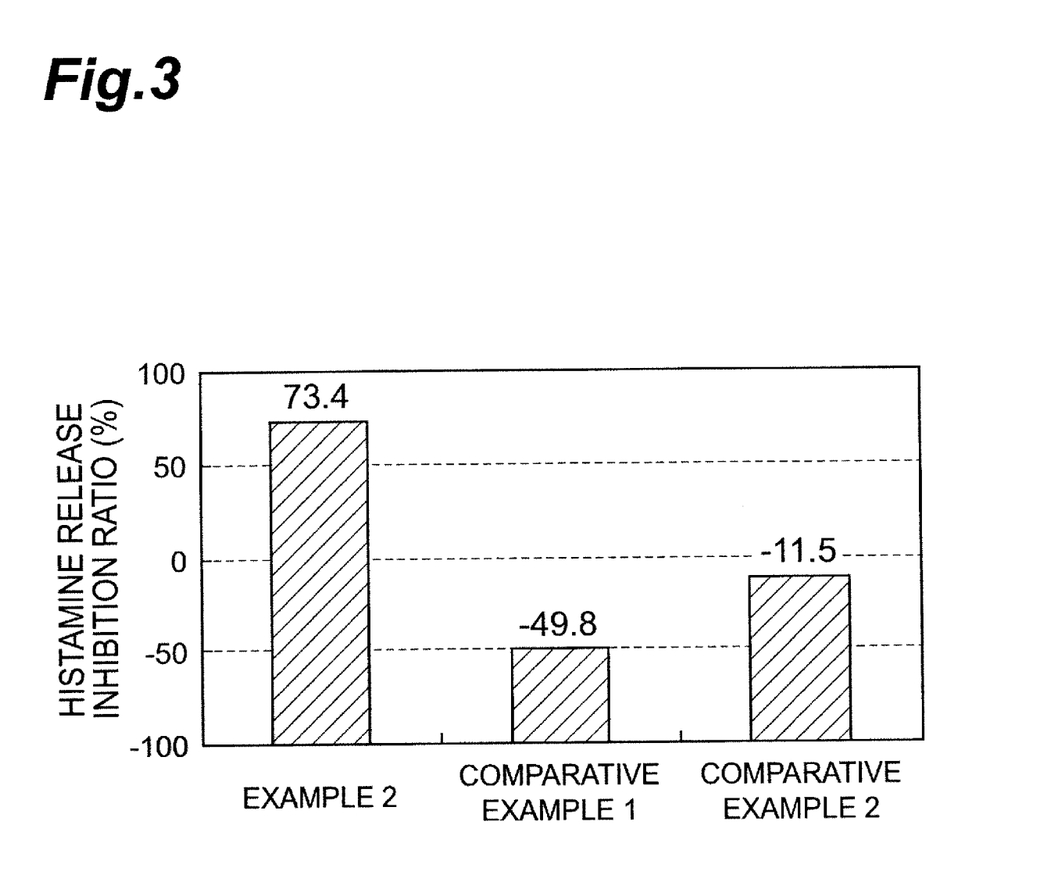
FIG. 3 shows the inhibitory effect (%) of the hop extracts obtained in Example 2 and Comparative Example 1-2 on histamine release from human basophiles.

The histamine release inhibition (%) for a hop cold-water extract obtained under the same conditions as Example 2 and the hop extracts obtained in Comparative Examples 1-2 are shown in FIG. 3. As shown in FIG. 3, a very high percentage of histamine release inhibition was obtained with the hop cold-water extract obtained under the same conditions as Example 2, but no histamine release inhibition was found with the chloroform-methanol extract (Comparative Example 1) or the hot water extract (Comparative Example 2).

Comparative Examples 3-5

After placing 100 g of hop pellets (Czech Saaz: type 90) in 1 L of distilled water, boiling for 15 minutes, 30 minutes and 60 minutes and centrifuging at 7000 rpm for 15 minutes, the supernatant was collected to obtain the extract (hot water extract). The extract obtained at 15 minutes was used for Comparative Example 3, the extract obtained at 30 minutes was used for Comparative Example 4, and the extract obtained at 60 minutes was used for Comparative Example 5.

Figure 4:
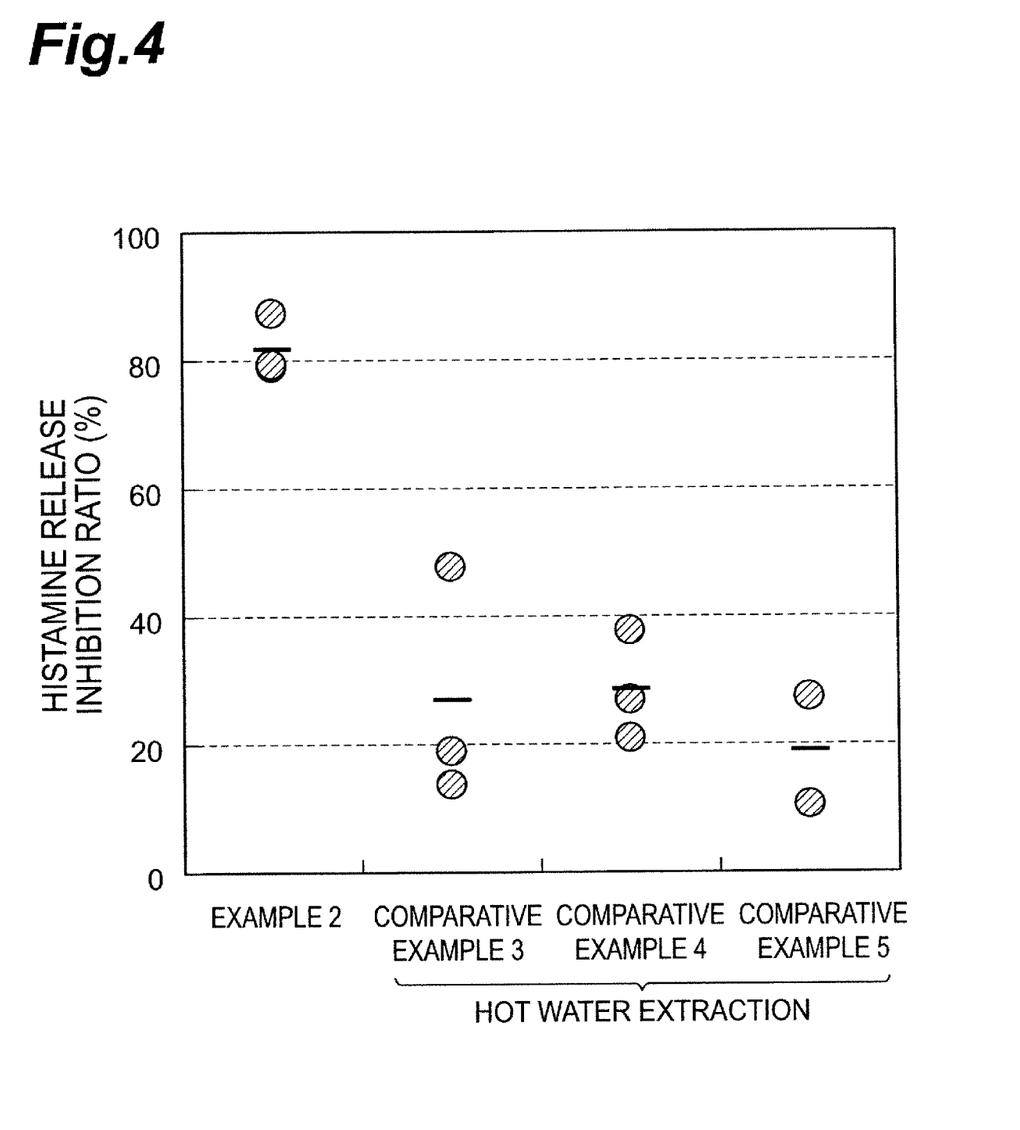
FIG. 4 shows the inhibitory effect (%) of the hop extracts obtained in Example 2 and Comparative Example 3-5 on histamine release from human basophiles.

The cold-water extract obtained under the same conditions in Example 2 and the hot water extracts of Comparative Examples 3-5 were used to determine the histamine release inhibition (%) in the manner described above. The results are shown in FIG. 4 (individual data represented by circles, and average values indicated by bars). As shown in FIG. 4, the histamine release inhibition rate of the cold-water extract was about 2-3 times superior to the hot water extracts.

Figure 5:
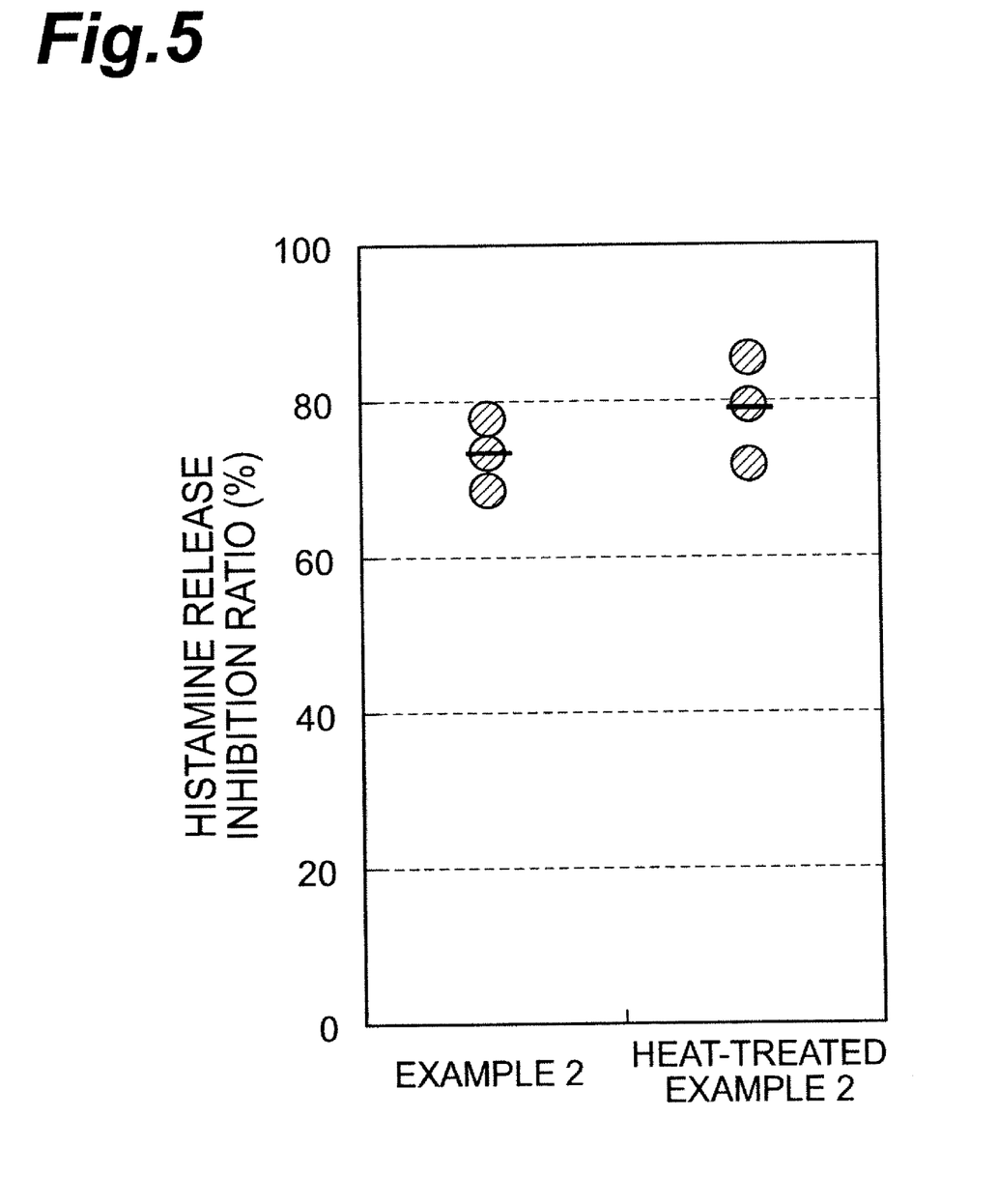
FIG. 5 shows the inhibitory effect (%) of the cold-water extract of Example 2 and a heat treated product of the cold-water extract of Example 2 on histamine release from human basophiles.

The following experiment was conducted in order to determine whether or not the reason for the low histamine release inhibition (%) in Comparative Examples 3-5 was inactivation by heat. Specifically, the cold-water extract obtained under the same conditions as Example 2 and a heat treated extract (100° C., 30 min) were measured to determine the histamine release inhibition (%) in the same manner as above. The results are shown in FIG. 5 (individual data represented by circles, and average values indicated by bars). As shown in FIG. 5, the cold-water extract exhibited no loss of activity due to heat treatment. It was therefore concluded that the hot water extracts of Comparative Examples 3-5 differed from the cold-water extract of Example 2 in their active ingredients.

Examples 3-5

Figure 6:
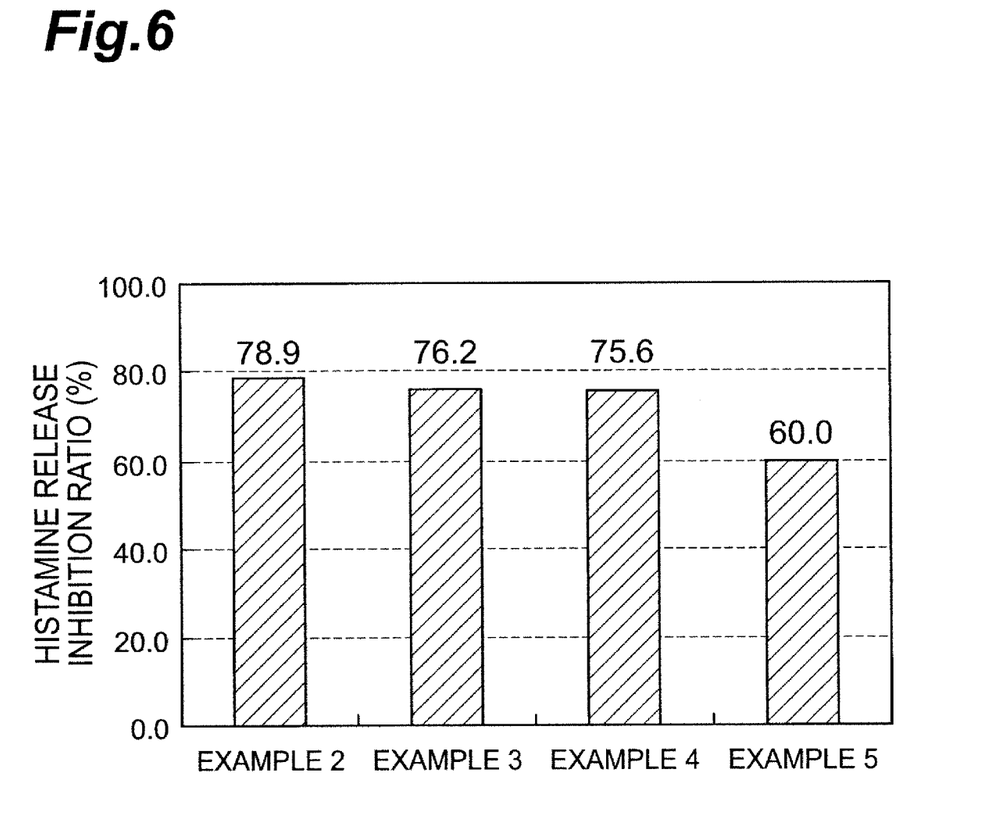
FIG. 6 shows the inhibitory effect (%) of the cold-water extracts of Examples 2-5 on histamine release from human basophiles.

The type of hop and tissue were changed to obtain cold-water extracts in the same manner as Example 1 or 2, and the histamine release inhibition (%) was calculated in the same manner as above. German Hallertauer Tradition pellets were used for Example 3, Kokusan Furano β pellets were used in Example 4, and Kokusan hop young leaves were used in Example 5. The results for the histamine release inhibition (%) are shown in FIG. 6. The same hops as in Example 2 (Czech Saaz pellets) are also listed in FIG. 6 as Example 2. As shown in FIG. 6, the superior hop varieties were Czech Saaz, German Hallertauer Tradition and Kokusan Furano β, and their leaves also had superior tissue.

Example 6

Inhibiting Action of Hop Water Extract on DNP-HSA-Induced Auricular Edema in Mice:

Six-week-old ICR mice (male or female; Charles River Laboratories, Japan Inc.) were separated into 4-5 per cage and raised at room temperature (24±2° C.) and 55±15% humidity, with a 12 hour light/dark cycle (light: 8:00-20:00). After preparatory rearing for at least one week, they were provided for the test. A hop pellet water extract, hop leaf water extract or ketotifen fumarate aqueous solution (10 mL/kg) was forcedly administered orally to each test group, while 10 mL/kg of distilled water was forcedly administered orally to the control group. The hop pellet water extract was prepared by adding hop pellets (Czech Saaz) to distilled water to 10% (w/w) and extracting overnight at 4° C., and then centrifuging at 3000 rpm for 10 minutes and filtering. The hop leaf water extract was prepared by adding dry hop leaves (Kokusan hop young leaves) to distilled water to 10% (w/w) and extracting overnight at 4° C., and then centrifuging at 3000 rpm for 10 minutes and filtering. The ketotifen fumarate aqueous solution was prepared by dissolving in distilled water to a concentration of 0.5 mg/mL.

At 1 hour after oral administration, 20 μL of 10 μg/mL mouse anti-DNP-IgE antibody (Sigma) was intradermally injected into one auricle of each mouse, while 20 μL of physiological saline (PS) was intradermally injected into the other auricle. At 24 hours after intradermal injection, 100 μL of 1 mg/mL DNP-HSA (antigen) was injected through the caudal vein. The auricular thickness before antigen administration and 30 minutes after antigen administration was measured three times each using a thickness gauge, and the auricular edema ratio and auricular thickness increase were determined. Significance testing between the groups was conducted by t-test. The auricular edema ratio (%) was calculated by the formula: (Mean auricular thickness 30 minutes after antigen administration−mean auricular thickness before antigen administration)×100/mean auricular thickness after antigen administration, and the auricular thickness increase (mm) was calculated by the formula: Mean auricular thickness 30 minutes after antigen administration−mean auricular thickness before antigen administration.

Figure 7:
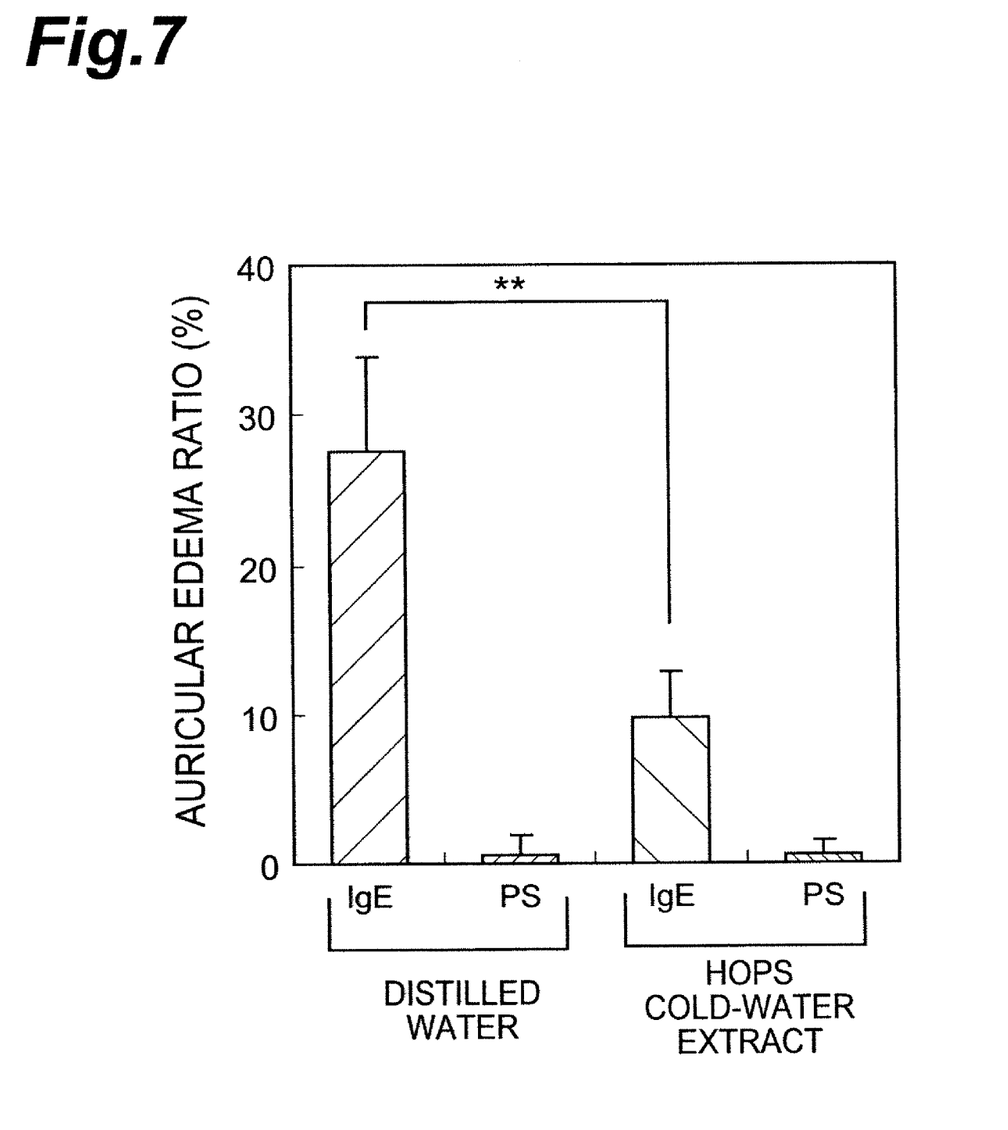

FIG. 7 shows the auricular edema ratios for mice that were orally administered distilled water and hop (Czech Saaz) water extract. (PS in FIG. 7 stands for "physiological saline"). In the distilled water oral administration group, the auricular thickness increase was 0.081±0.019 mm with intradermal injection of IgE antibody, and the auricular edema ratio was 31.1±6.4 (%). In the hop pellet water extract oral administration group, the auricular thickness increase was 0.019±0.010 mm with intradermal injection of IgE antibody, and the auricular edema ratio was 9.7±3.2 (%). The hop pellet water extract-administered group had a significantly inhibited auricular edema ratio compared to the distilled water-administered group (p<0.01). In contrast, no increase in auricular thickness was found with intradermal injection of physiological saline (PS) to either the control group or the test groups.

Figure 8:
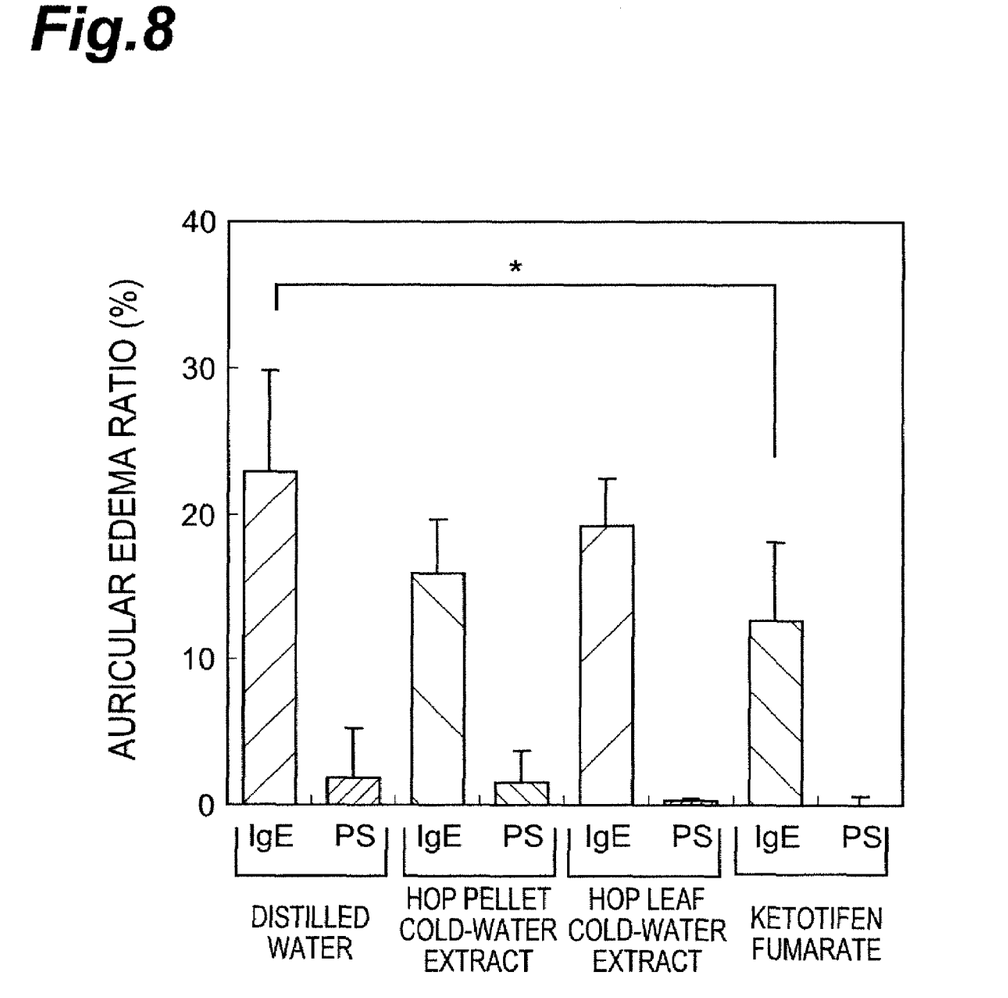
FIG. 8 shows the effect of distilled water, hop pellet cold-water extract, hop leaf cold-water extract, and ketotifen fumarate on the increase of ear thickness of mouse induced by a passive cutaneous anaphylaxis.

FIG. 8 shows the auricular edema ratios for mice that were orally administered distilled water, hop pellet water extract, hop leaf water extract or ketotifen fumarate aqueous solution. In the distilled water oral administration group, the auricular thickness increase was 0.081±0.024 mm with intradermal injection of IgE antibody, and the auricular edema ratio was 22.9±6.8%. In the group administered an aqueous solution of the chemical mediator release inhibitor ketotifen fumarate, however, the auricular thickness increase was 0.045±0.020 mm with intradermal injection of IgE antibody, and the auricular edema ratio was 12.7±5.4%. The ketotifen fumarate aqueous solution-administered group had a significantly inhibited auricular edema ratio compared to the distilled water-administered group (p<0.05). On the other hand, the hop pellet water extract-administered group and hop leaf water extract-administered group exhibited no statistically significant difference compared to the distilled water-administered group (critical region: 5%), but inhibition in auricular edema was suggested (p value of 0.08).

The invention claimed is:

1. A purified composition comprising a histamine release inhibiting effective amount of a cold-water extract of hop tissue, wherein the purified composition is produced by a process comprising immersing the hop tissue in water at above 0° C. and no higher than 10° C. to produce an extracted solution comprising an extracted tissue, and separating the extracted tissue from the extracted solution to form the purified composition.

2. The purified composition of claim 1, wherein the purified composition comprises at least one of quercetin malonylglucoside, rutin, and/or isoquercetin.

3. The purified composition of claim 1, wherein the purified composition comprises quercetin malonylglucoside, rutin, and isoquercetin.

4. The purified composition of claim 1, wherein the temperature of the cold water is from 2° C. to 8° C.

5. The purified composition of claim 1, wherein the hop tissue is at least one of a stem, a leaf, and/or a cone.

6. The purified composition of claim 3, wherein the temperature of the cold water is from 2° C. to 8° C.

* * * * *